United States Patent [19]

Weinshenker

[11] 3,959,190

[45] May 25, 1976

[54] INSOLUBLE OXIDATION REAGENT

[75] Inventor: Ned M. Weinshenker, Palo Alto, Calif.

[73] Assignee: Dynapol, Palo Alto, Calif.

[22] Filed: June 17, 1974

[21] Appl. No.: 479,654

[52] U.S. Cl. .................... 260/2.5 HB; 260/2.5 B; 260/2.5 R; 260/79.5 NV; 260/598
[51] Int. Cl.² .................... C08J 9/36; C08F 28/04
[58] Field of Search..... 260/2.5 HB, 2.5 R, 79.5 NV

[56] References Cited
UNITED STATES PATENTS

| | | | |
|---|---|---|---|
| 2,469,132 | 5/1949 | Schulze | 260/79.5 NV |
| 2,543,844 | 3/1951 | Fryling | 260/79.5 NV |
| 2,543,867 | 3/1951 | Pritchard | 260/79.5 NV |
| 2,556,856 | 6/1951 | Swaney et al. | 260/79.5 NV |
| 3,342,790 | 9/1967 | de Vries | 260/79.5 NV |
| 3,655,618 | 4/1972 | Weil | 260/79.5 NV |

OTHER PUBLICATIONS

"Specialty Chemicals for Research & Industry" Haven Chemical, 5000 Langdon St., Phila., Pa. 19124.

*Primary Examiner*—Morton Foelak
*Attorney, Agent, or Firm*—William H. Benz

[57] ABSTRACT

A polymeric sulfide oxidation reagent comprising a cross-linked polymeric resin carrying a plurality of lower alkyl sulfide groups, its preparation and its use as a co-reactant for the oxidation of primary and secondary alcohols are disclosed.

7 Claims, No Drawings

INSOLUBLE OXIDATION REAGENT

Background of the Invention

1. Field of the Invention

This invention relates to polymeric reagents for the oxidation of alcohols; more particularly, it relates to polymeric sulfide oxidation reagents.

2. The Prior Art

Sulfur-containing materials are finding increasing use as oxidation reagents. U.S. Pat. No. 3,444,216 to Parikh and Doering discloses the use of a hydrocarbonsulfoxide such as dimethylsulfoxide with tertiary amines to effect alcohol oxidation. Similarly, the Corey oxidation method (E. J. Corey and C. U. Kim, JACS, 94 7586 [1972]) employs thioanisole to oxidize alcohols. These methods offer advantages of mild conditions and simple operation. However, they also have disadvantages. First, many of the sulfur-containing reagents are fluids, either gas or liquid, which are very odiferous. It is thus difficult to work with these materials except in hoods and the like, and often difficult to remove residual traces of "sulfide smell" from products. Also, it is generally not possible to simply separate conventional sulfide reagents from reaction mixtures for regeneration and reuse or on an industrial scale to avoid sulfur contamination of waste streams, problems which are growing in importance as feedstock scarcity and ecological concerns become ever more pressing.

The present invention offers a new type of sulfur oxidation reagent which avoids, to a major extent, the failings of the prior art while substantially retaining the advantageous reactivity of known sulfide reagents.

Statement of the Invention

It has now been discovered that a certain group of polymeric oxidation reagents solves the problem of the prior art and functions with excellent efficiency in the conversion of alcohols to carbonyls. These reagents have an organic solvent-insoluble cross-linked organic resin backbone. Covalently attached directly to carbon atoms of this backbone are a plurality of lower alkyl sulfide groups. These reagents may be depicted by General Formula (I)

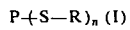

$$P\text{-}(S\text{---}R)_n \quad (I)$$

wherein P is the backbone, R is lower alkyl, and n is a number greater than 1, preferably such that the reagent contains from 1 to 10 mmoles of sulfur per gram.

Description of the Preferred Embodiments

The Sulfur-Containing Groups

The present reagents have sulfur-containing groups. These groups (—S—R in General Formula I) are alkyl sulfide groups, which might also be defined as alkylthioethers. The alkyl group, R, is a lower saturated alkyl, suitably of from 1 to about 5 carbon atoms, and may include methyl, and ethyl groups and the propyl groups, both iso and normal, and the several butyl and pentyl (amyl) groups. While any of these lower alkyls alone or in mixtures, one with another, are suitable, the methyl group is the preferred alkyl substituent.

The Polymer Backbone

The polymer backbone, P, is a cross-linked polymeric organic resin, preferably a macroreticular cross-linked polymeric organic resin. The term "macroreticular" defines that the resin is macroporous and that it has a high specific surface area. The pores should have average diameters of at least 100 A. The specific surface area (measured by the B.E.T. method) should be at least about 1 M²/g. Preferably, pore diameters have an average value of from about 200 A to 2,000 A, while specific surface areas preferably range from about 5 M²/g to 300 M²/g. The polymer backbones may include polyalkyl materials such as polypropylene, polyethylene, or polycyclopentadiene, and polyaromatic materials such as polystyrene, polymethylstyrene, and the like. Polystyrene is preferred as a backbone polymer. Not only does it offer a chemically excellent substrate to which to attach the sulfide groups, but it also is readily available in forms very suited for reagent use.

The backbone polymer is cross-linked. This ensures the reagent's insolubility in all conventional organic media such as hydrocarbons (e.g., hexane or cyclohexane), ketones (e.g., acetone), or ethers (e.g., THF or diethylether). In accordance with this invention, a reagent is to be considered "insoluble" if its solubility in the organic reaction media is less than 0.1% basis reaction media. Suitably the backbones contain from 0.1 to 10 cross-links for each 100 carbon atoms. These cross-links can occur directly between polymer chains or they can be effected via added linking groups. In the case of the preferred polystyrene backbones, a simple and preferred way to introduce cross-links is to copolymerize minor amounts of divinylbenzene with the styrene. Generally, amounts of divinylbenzene ranging from 0.2 to about 8% (basis styrene) are useful, with amounts of from about 0.5% to about 5% being preferred.

The macroreticular structure of the polymeric backbone offers a number of distinct advantages: (1) Its porous nature provides access to the inner areas of solid particles of reagent, both to sulfide groups when forming the reagent and to reactants when the reagents are being used; (2) It has a solid (not gel) structure, so it is easy to separate; and (3) It undergoes only moderate swelling in organic media.

Alkyl Sulfide Content

The alkyl sulfide groups are covalently attached to the polymer backbone directly through a thioether linkage. In the case of the preferred polystyrene backbones, this attachment is directly from the sulfur atoms to carbons on the aromatic ring, preferably the aromatic carbons which are para to the links between the styrenes. In many applications it is desirable that as many alkyl sulfide groups are incorporated into these reagents as possible. The number of sulfide groups incorporated into the reagents should be controlled. As will be shown in the section captioned "Use of the Reagents", the performance of these reagents varies, as does the product yield, depending upon the sulfide content. Generally, sulfide group contents of at least 0.1 mmole/gram are suitable, with a maximum of about 10 mmoles/gram being achievable. In the case of polystyrene-based materials, 6.7 mmoles of sulfide/gram of reagent is equivalent to 1.0 sulfide groups attached to each aromatic ring, and it is preferred to have between about 0.2 and 6.7 mmoles of sulfide present per gram of these reagents.

Preparation

Conceptually, these reagents can be prepared either by forming a monomeric alkyl sulfide and then polymerizing it into the desired polymer product, or by taking a preformed polymeric backbone and so treating it to covalently attach the sulfide groups via thioether links. Both routes are within the purview of this invention. In practice, because of the desire to have backbones of set characteristics, it is generally preferred to use the preparation wherein a preformed polymer is treated. An exemplary method for this preparation involves first brominating a suitable polymer with molecular bromine in the presence of a catalyst such as thallic acetate sesquihydrate or ferric chloride, and thereafter treating the brominated polymer with a metal alkyl such as n-butyllithium and with methyldisulfide to afford the polymeric sulfide reagent. This sequence will be elaborated upon in the Examples, but is presented merely as a representative preparative scheme. Other methods, possibly of even greater industrial efficiency, might be pursued as well.

Use of the Reagents

In one application, these polymer reagents function as an effective replacement for thioanisole in the Corey oxidation method for alcohols. In this application, the alcohol is oxidized as follows: First, a reagent of this invention, $P-(S-R)_n$, is contacted with at least a molar equivalent of a sulfonium ion generator such as molecular halogen, preferably chlorine as shown, to yield a charged sulfonium ion addition product, such as $P-(S^+-R)_n$, plus n anions ($X^-$) such as halide ions, $Cl^-$. This may be most easily carried out in liquid reaction media such as dichloromethane, tetrahydrofuran, or ethylacetate, at low to moderate temperatures such as from about $-100°C$ to about $20°C$ for periods of from about 0.1 hours to about 2 hours, although longer times may be used if desired.

In a second step, the charged sulfonium ion addition product is intimately contacted with the alcohol to be oxidized, $R'-CH_2OH$, to form a charged alcohol addition product,

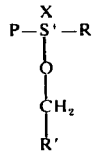

plus the protonated form of the sulfonium ion generator, in the case of the halides, hydrogen halide. Generally, this step is carried out at low to moderate temperatures ($-100°C$ to about $20°C$) and generally requires 0.5 to about 20 hours. It may be carried out in the same vessel used for the first step without isolation of intermediates, if desired.

When this charged alcohol addition product is treated with a molar excess of a base, such as a triethylamine, the alcohol oxidation product, $R'-CHO$, is liberated along with the starting polymeric reagent and the halogen salt of the base. The base is added to the reaction mixture in a separate step after the alcohol is added. This step is very rapid, requiring only from 0.01 to 0.5 hours, and may be carried out at room temperature or any temperature from about $-50°C$ to $+100°C$.

After use, the reagent may be simply washed, recovered by filtration or decantation, and reused. The usefulness of the reagents of this invention is not limited to any particular co-reactants. In place of chlorine may be used any material which when contacted with the reagent of this invention functions as a generator of sulfonium ions. Halogens, such as bromine or fluorine, are useful, as are N-derivatives of succinimide, such as N-chlorosuccinimide, N-acetoxysuccinimide, N-trifluoroacetoxysuccinimide and the like. In place of triethylamine, other bases capable of forming a salt with the acid generated in the reaction can be used, including trimethylamine or other trialkylamines; other organic bases, such as pyridine, lutidine, and collidine; and inorganic bases such as sodium or potassium or ammonium hydroxide. Among the co-reactants, however, chlorine and organic bases, especialy trialkylamines, are preferred.

Alcohols which may be oxidized by use of the present reagent include primary and secondary alcohols. Thus the alcohols treated include the simple lower alkanols, such as n-butanol and sec-butanol, or the like; aromatic alcohols such as benzyl alcohol; primary and secondary alcohols having various other functional groups present (such as $NO_2$, $COOR$, $CN$, etc.); and more complex alcohols such as prostaglandin alcohol, 3–4(methoxyphenyl)-propan-1-ol, and the like. While an exhaustive list of alcohols could be here presented, in the interest of brevity these few representative materials must suffice. It should not be taken as limiting the applicability of the present reagents in any way, as it appears that the reagents can oxidize virtually any primary alcohol to an aldehyde or any secondary alcohol to a ketone.

The reactions are carried out in a liquid phase, which contacts the solid reagents. The solid reagent may be present as a fixed bed of particles or preferably is present as a slurry of particles in the reaction medium. In either case, the reagent is in the form of particles of from about 0.2 mm to about 1 cm in size, preferably from about 0.5 mm to about 5 mm in size.

The amount of reagent employed should be at least equal in molar amount to the amount of alcohol being oxidized, as one mole of reagent is employed for each mole of oxidation. Generally, an excess of reagent is employed. Preferably from 1.1 to about 6.0 moles of reagent is employed for each mole of alcohol to be oxidized.

A special application of these reagents involves the partial oxidation of polyols. It has been surprisingly found that under certain conditions polyols are only partially oxidized, so that for example only one alcohol group is oxidized to a carbonyl. This makes the formation of carbonyl and alcohol group-containing materials possible, something not easily done by conventional oxidations of alcohols or reductions of carbonyls. As a rule, best "monooxidation" results are obtained with reagents which have relatively lower concentrations of sulfur atoms, such as from about 2.0 mmoles of sulfur/gram to about 0.1 mmoles of sulfur/gram, and preferably from about 1.5 mmoles of sulfur/gram to about 0.15 mmoles of sulfur/gram.

During the oxidations several advantages are apparent: first, there is no odor to the reagents; second, reaction takes place at very mild conditions; third, the reagent may be very easily recovered after use by settling, filtering, or any other solid-liquid separation scheme.

The invention will be further illustrated by the following Examples. These are intended merely to illustrate the invention and are not to be taken as limiting its scope, which is instead defined by the appended claims.

EXAMPLE I

A. Preparation of poly (p-bromostyrene)

The procedure of F. Camps et al., Tet Let 1713–14 (1971), was followed. To 13.0 g (125 mmoles) of macroreticular polystyrene (Amberlite XE-305, Rohm-Haas) and 27.6 g (67.5 mmoles) of thallic acetate sesquihydrate [Tl(OAc)$_3$·1.5 H$_2$O] suspended in 200 ml of carbon tetrachloride was added dropwise with stirring 12.8 (4.1 ml; 80 mmoles) of bromine (as Br$_2$) in 30 ml of carbon tetrachloride and the mixture then stirred at 50°–60° until all bromine color disappeared. The beads were filtered and washed with the following: (1) a mixture (1:1) of 30% aqueous HCl and dioxane; (2) a mixture (1:1) of water and dioxane; (3) dioxane; (4) THF; and (5) ether. The air-dried beads were further dried in vacuo (ca. 0.1 mm/Hg) at 50°–60° overnight. The polymer weighed 21.2 g (82.0% yield). The brominated polystyrene was refluxed in 500 ml of 0.1 N aqueous HCl solution, then in 50% aqueous dioxane and finally in dioxane. The elemental analysis of vacuum dried (ca. 0.1 mm Hg) beads indicated 65% of the theoretical bromine (3.56 mmoles Br/g).

B. Preparaton of Poly (p-methylmercaptostyrene)

To a stirred suspension of 14.5 g (51.6 mmoles) of poly (p-bromostyrene) in tetrahydrofuran (200 ml) was added at −78°C under argon 50 ml of 2.28 M n-butyllithium hexane (114 mmoles) solution and the stirring was continued at −78°C for 0.5 hr. and then at room temperature for 1 hour. The tetrahydrofuran solution was drawn from the polymer by syringe. The beads were recharged at −78°C with 150 ml of THF and 30 ml of 2.28 M n-butyllithium (68.4 mmoles), and stirred at room temperature for 1 hour. The tetrahydrofuran was removed again, whereupon the polymer beads were treated with 200 ml THF and 20 ml of methyldisulfide (distilled), stirred at −78°C for 15 minutes and at room temperature for one-half hour and then refluxed under argon for 1 hour. The cooled mixture was diluted with 100 ml of water and filtered. The beads were washed with the following solvents: (1) water; (2) a 3:1 mixture of dioxane/water; and (3) dioxane. Finally, the beads were refluxed in dioxane for one-half hour and the dioxane was distilled off until the distillate reached the boiling point (100°C) of dioxane. The elemental analysis of the vacuum-dried beads (70°C, overnight), 11.4 g, gave 54% of the theoretical sulfur incorporation (3.56 mmoles S/g).

C. Oxidation Reactions of the Alcohols Employing Poly (p-Methylmercaptostyrene)

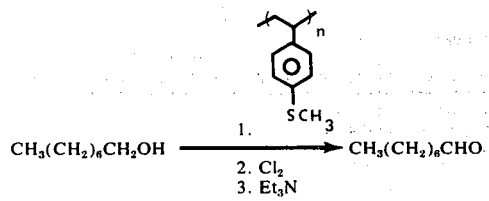

$$CH_3(CH_2)_6CH_2OH \xrightarrow[\substack{2.\ Cl_2 \\ 3.\ Et_3N}]{1.\ \text{SCH}_3\text{-polymer}} CH_3(CH_2)_6CHO$$

To a stirred suspension of 1.0 g (3.56 equivalents of sulfide group) of poly (p-methylmercaptostyrene) in dichloromethane (20 ml) was added at −10°C a solution of 280 mg (3.94 mmoles) of chlorine (as cl$_2$) in 10 ml of CH$_2$Cl$_2$, after which the mixture was cooled to −78°C, treated with 130 mg (1 mmole) of octanol in 1.6 ml of CH$_2$Cl$_2$, and stirred at −78°C for 0.5 hr., and then −25°C for 4.5 hours. The reaction mixture was treated at −25°C with 612 mg (6 mmoles) of triethylamine in 2 ml of CH$_2$Cl$_2$ and stirred for an additional 20 minutes. Ether (50 ml) was next added, and after stirring for 10 minutes, the resulting mixture was filtered and the beads washed with another 30 ml of ether. The combined filtrate was next washed with 1 N HCl solution and brine, and dried (MgSO$_4$). After removal of the solvent by evaporation under reduced pressure, the product was evaporatively distilled (bulb to bulb) at an oven temperature of 50°C and 0.1 mm pressure to yield 122 mg (95%) of octanal. GLC analysis (4% SE-30) of the product indicated the presence of 97% octanal and 3% starting material.

The polymeric beads recovered from the above reaction are washed thoroughly with 1:1 dioxane/1 N HCl, 1:1 dioxane/H$_2$O, dioxane, and dried on the filter funnel. The beads were reused. After five reuses they retained substantially all of their original activity.

EXAMPLE II

The preparation of Example I, parts A and B, was repeated, substituting ferric chloride for thallic acetate as catalyst. The final product contained 3.61 mmoles of sulfur per gram.

EXAMPLE III–VI

The preparation of Example I, parts A and B, was repeated, varying the amount of methyldisulfide used. Final products containing 5.0, 3.3, 1.13, and 0.55 mmoles of sulfur per gram of reagent were obtained.

EXAMPLES VII–IX

The preparation of Example I, parts A and B, is repeated, varying the starting polymeric resin. Macroporous polymethylstyrene, polypropylene, and polycyclopentadiene are employed and yield final products containing about 3 mmoles of sulfur per gram.

EXAMPLES X–XI

The preparation of Example I is repeated, substituting other sulfur-containing materials for methyldisulfide. Ethyldisulfide and propyldisulfide and pentyldisulfide are employed, yielding products wherein R (in Formula I) is ethyl, propyl and pentyl respectively.

EXAMPLES XI–XVI

A variety of alcohols was oxidized using the reagents of Examples I, III and IV, and the general procedure of Part C of Example I.

Prostaglandin alcohol was oxidized to the corresponding aldehyde in 90% yield in 4 hours (.2 hours for Step I, 4 hours for the reaction with alcohol) with the reagent of Example II.

3-(4′-methoxyphenyl)-propan-1-ol was oxidized to 3-(4′-methoxyphenyl)-propan-1-al in 94% yield in 4 hours with the reagent of Example III.

4-phenylcyclohexanol was oxidized to 4-phenylcyclohexanal in 90% yield in 4 hours with the reagent of Example I.

Benzyl alcohol was oxidized to benzaldehyde in 67% yield in 5 hours (0.2 hours toe the chlorine reaction step) with the reagent of Example IV.

EXAMPLES XVII–XXIV

A series of oxidations of 1-octanol are carried out using the reagent of Example V and a reagent in accord with Example I containing 2.45 mmoles of sulfur per gram. N-chlorosuccinimide was employed as the sulfonium ion forming material in place of chlorine. Reaction conditions were varied. The results of these reactions are given in Table I.

method and reagents of Example I, Example IV, and Example VI. By varying the sulfur content of the reagent, a varying degree of monoaldehyde oxidation selectivity was achieved, as shown in Table II.

TABLE I

OXIDATION WITH N-CHLOROSUCCINIMIDE

| Exp. No. | (mmol) | (mmol) Sulfur per gram Resin | NCS (MW = 133.5) (mmol) | Oc- tanol (mmol) | Solvent (%CH$_2$CL$_2$ in Toluene) | A- mount of Solvent (ml) | Step 1 Reaction* Temp (°C) | Reaction Time | Step 2 Reaction* Temp (°C) | Reaction Timr (hr) | % Aldehyde | Products & % Alkyl Chloride | % Unreacted Alcohol |
|---|---|---|---|---|---|---|---|---|---|---|---|---|---|
| 17 | 10.0 | 2.45 | 10.0 | 2.0 | 100 | 46 | −25 | 20 min | −40 | 6 | 58 | 42 | 0 |
| 18 | 2.5 | 2.45 | 2.5 | 0.5 | 50 | 46 | −25 | 20 min | −40 | 6 | 75.2 | 24.8 | 0 |
| 19 | 5.0 | 2.45 | 5.0 | 1.0 | 50 | 32 | 0 | 1 hr | −40 | 4 | 75.3 | 24.7 | 0 |
| 20 | 2.5 | 2.45 | 2.5 | 0.5 | 30 | 56 | 0 | 1 hr/ 20 min | −40 | 6 | 39.4 | 12.6 | 52 |
| 21 | 2.5 | 2.45 | 2.5 | 0.5 | 25 | 56 | 0 | 20 min | −40 | 6 | 20.8 | 4.2 | 75 |
| 22 | 2.5 | 2.45 | 2.5 | 0.5 | 15 | 66 | 0 | 1 hr | −40 | 6 | 52.7 | 8.4 | 38.9 |
| 23 | 2.5 | 2.45 | 2.5 | 0.5 | 15 | 10 | 0 | 17 hr | −40 | 6 | 0 | 0 | 100 |
| 24 | 5.7 | 1.13 | 516 | 1.0 | 0 | 50 | 0 | 15 min | −25 to −35 | 6 | 23.4 | 0 | 76.6 |

TABLE II

SELECTIVE OXIDATION OF 1,7-HEPTANEDIOL*

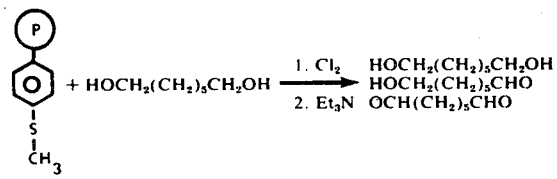

| Exp. No. | Concentration of Sulfide Moiety in the Polymer | Total mmole of Sulfide Used | Amount of Chlorine as Cl$_2$ | Reaction Time (hr) | Percent of Product | | | Conversion Selectivity Monoaldehyde/mono+dialdehyde |
|---|---|---|---|---|---|---|---|---|
| | | | | | Monoaldehyde | Dialdehyde | Diol | |
| 25 | 3.56 mmol S/g | 3.56 | 3.56 | 4 | 44.3 | 40.3 | 15.4 | 52 |
| 26 | 1.13 mmol S/g | 4.75 | 2.40 | 6 | 56.7 | 28.1 | 15.2 | 66 |
| 27 | 1.13 mmol S/g | 1.70 | 1.70 | 6 | 46.8 | 7.5 | 45.7 | 86 |
| 28 | 1.13 mmol S/g | 1.13 | 1.13 | 6 | 36.4 | 5.0 | 58.6 | 87 |
| 29 | 0.66 mmol S/g | 2.00 | 2.00 | 6 | 50.2 | 2.2 | 47.6 | 95 |
| 30 | 0.66 mmol S/g | 2.64 | 2.00 | 19 | 50.6*** | 5.0 | 0.5 | 91 |

*One mmole of diol was used in each reaction.
***The remaining material (43.9%) was unidentified byproducts.

EXAMPLES XXV–XXIX

The oxidation of 1,7,-heptanediol was carried out under varying reaction conditions using the general

What is claimed is:
1. A polymeric sulfur reagent comprising a solid organic solvent-insoluble macroreticular cross-linked polystyrene resin backbone having lower alkyl sulfide groups covalently attached directly to carbon atoms thereof through thioether linkages.

2. The reagent of claim 1, wherein the lower alkyl sulfide groups each contain from 1 to 5 carbons atoms.

3. The reagent of claim 2, wherein the lower alkyl sulfide groups are present in an amount of from about 0.1 mmole/gram of reagent to about 10 mmoles/gram of reagent.

4. The reagent of claim 3, wherein the alkyl sulfide groups are attached to the polystyrene aromatic carbons para to the attachment between the styrenes through thioether linkages.

5. The reagent of claim 4, wherein the lower alkyl sulfide group is methyl sulfide.

6. The reagent of claim 5, wherein the methyl sulfide groups are present in an amount of from 0.1 mmoles/gram of reagent to about 1.0 mmoles/gram of reagent.

7. The reagent of claim 5, wherein the methyl sulfide groups are present in an amount of from about 1.0 mmoles/gram of reagent to about 6.7 mmoles/gram of reagent.

* * * * *